(12) United States Patent
Chen

(10) Patent No.: US 6,261,267 B1
(45) Date of Patent: *Jul. 17, 2001

(54) AUTOMATIC IV SHUT OFF VALVE

(75) Inventor: Wei Chen, Houston, TX (US)

(73) Assignee: Globe Enterprises, Inc., Houston, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/169,732

(22) Filed: Oct. 9, 1998

(51) Int. Cl.[7] ..................................................... A61M 5/00
(52) U.S. Cl. ........................... 604/247; 604/254; 604/414
(58) Field of Search .................................... 604/245, 246, 604/247, 251, 254, 405, 411, 414

(56) References Cited

U.S. PATENT DOCUMENTS

| | | | |
|---|---|---|---|
| 3,656,505 | * 4/1972 | O'Brian | 128/214 |
| 3,776,229 | * 12/1973 | McPhee | 128/214 C |
| 4,055,176 | * 10/1977 | Lundquist | 128/214 C |
| 4,175,558 | * 11/1979 | Hess, III et al. | 128/214 C |
| 4,959,053 | * 9/1990 | Jang | 604/411 |
| 5,098,407 | * 3/1992 | Okamura | 604/248 |
| 5,423,346 | * 6/1995 | Daoud | 604/254 |
| 5,533,647 | 7/1996 | Lang-Hsiang | 222/83 |
| 5,722,961 | 3/1998 | Fan | 604/354 |
| 5,730,730 | * 3/1998 | Darling, Jr. | 604/246 |

* cited by examiner

Primary Examiner—Anhtuan T. Nguyen
Assistant Examiner—Jeremy Thissell
(74) Attorney, Agent, or Firm—Richard L. Moseley

(57) ABSTRACT

An IV container spike and drip chamber assembly is provided that includes an automatic shut off mechanism which allows nurses to change the fluid container without removing the catheter from the patient. The automatic shut off mechanism comprises a floating ball capable of being supported by or floating in the fluid due to the buoyancy of the fluid. The IV container spike also includes an air vent which allows the air in the drip chamber to vent out directly when the nurses want to change the container of medicinal fluid. The air vent is closed for the initial use and during the infusion process. As the medicinal fluid is gradually reduced in level in the drip chamber, the floating ball is lowered thereby and when the floating ball reaches the bottom of the drip chamber, the floating ball blocks the outlet so as to stop the injection. After the injection is stopped nurses can take off the spike and insert it into a new medicinal fluid container, and open the air vent cap until the new medicinal fluid reaches the required level in the drip chamber. The air vent cap should be closed immediately after the medicinal fluid reaches the desired level.

2 Claims, 5 Drawing Sheets

AUTOMATIC IV SHUT OFF VALVE

BACKGROUND OF THE INVENTION

1. Field of the Invention

This invention relates to an intravenous (IV) spike for attachment to a container of a parenteral fluid. More particularly the invention relates to an IV spike and drip chamber having an automatic shut off mechanism which stops infusion into the patient when the container is empty. More particularly the invention relates to an IV spike and drip chamber having a shut off mechanism and a vent mechanism in the spike for removing air from the drip chamber when the container is changed.

2. Related Information

It is a common practice in treating patients, particularly patients who must be cared for under emergency conditions, to administer medications into the patient intravenously. An intravenous solution, commonly referred to as parenteral fluid, is fed from a container, bottle or I.V. bag, through a tubing and a catheter which has been inserted into the patient's vein. The catheter is secured to the patient by a strip of adhesive tape. The IV fluid container is punctured by a spike which often includes a drip chamber for calculating the flow rate and visual inspection that fluid is flowing (dripping) from the container into the tubing. In the past the container was monitored and when empty had to be changed. An automatic shut off mechanism in the drip chamber is preferred.

Automatic shut off mechanisms in IV container drip chambers are known in the art. See for example U.S. Pat. No. 5,722,961 to Fan. A problem arises with the spike disclosed therein when the container is changed. The air in the drip chamber cannot be removed. Generally the sides of the drip chamber are pressed inwardly to remove the air. However, the IV tubing must be disconnected from the patient to prevent the air from entering the vein. The shut off mechanism disclosed therein is also large and cumbersome in relation to the drip chamber and might become stuck in the open position in the chamber.

A standard IV spike with a vent for venting air into the container (bag or bottle) is disclosed in U.S. Pat. No. 5,533,647 issued to Lung Hsiung. This vent does not solve the problem of the air in the drip chamber when the container is changed.

SUMMARY OF THE INVENTION

An IV spike with drip chamber is provided that includes an automatic shut off mechanism which prevents air from entering the IV tube when the container is empty and allows nurses to change the fluid container without removing the catheter from the patient. The automatic shut off mechanism comprises a floating ball capable of being supported by or floating in the fluid due to the buoyancy of the fluid. The IV spike also includes an air vent which allows the air in the drip chamber to vent out directly when the nurses want to change the container of medicinal fluid. The air vent is closed for the initial use and during the infusion process. As the medicinal fluid is gradually reduced in level in the drip chamber, the floating ball is lowered thereby and the floating ball reaches the bottom of the drip chamber. The floating ball blocks the outlet so as to stop the injection. After the injection is stopped nurses can take off the spike and insert it into a new medicinal fluid container, and open the air vent cap until the new medicinal fluid reaches the required level in the drip chamber. The air vent cap should be closed immediately after the medicinal fluid reaches the required level.

If desired a second vent from the atmosphere back upward through the spike into the container may be provided for use with rigid IV bottles. The second vent is not necessary where the bag collapses as it empties.

DESCRIPTION OF THE PREFERRED EMBODIMENT

For a detailed description of the preferred embodiment the reader is directed to the accompanying figures in which like components are given like numerals for ease of reference.

Figure 1:
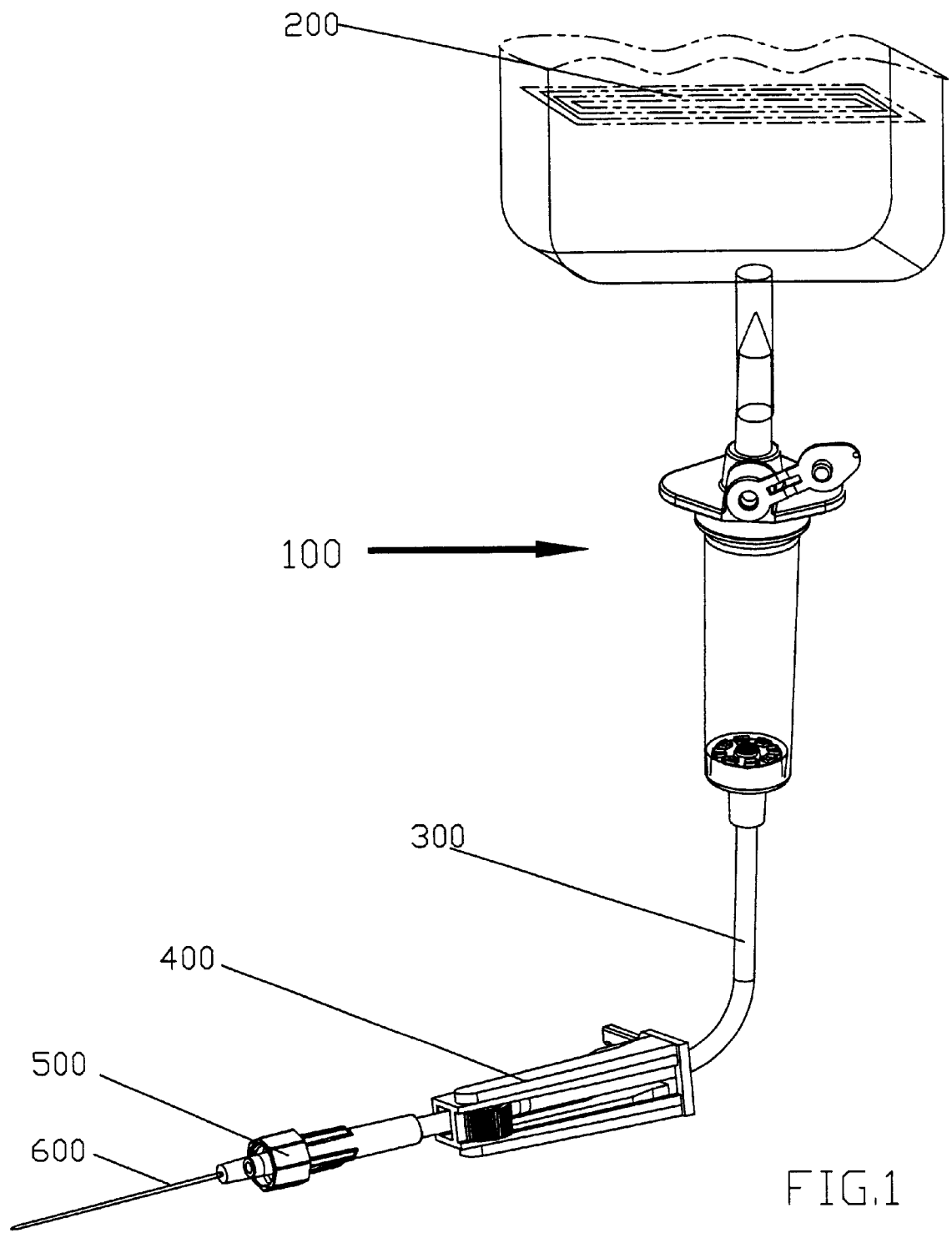
FIG. 1 is a schematic view of an I.V. system utilizing the spike and drip chamber assembly of the present invention.

Referring first to FIG. 1 there is shown an intravenous fluid administration system. The spike and drip chamber assembly 100 is shown inserted through the puncture pad in the lower end of the IV fluid container 200. A tube 300 is attached by one end to the bottom of the spike and drip chamber assembly 100. A roller clamp 400 is placed over the tube 300 to adjust and control the flow of fluid from the bag. The extreme end of the tube 300 is secured to the a luer connection 500 on a catheter 600 which is placed into the vein of the patient. Since the fluid is administered by gravity flow the direction up, down, upper and lower have definite meanings. Other apparatus which may be placed in the line such as a Y connector for administering additional drugs are not shown.

Figure 2:
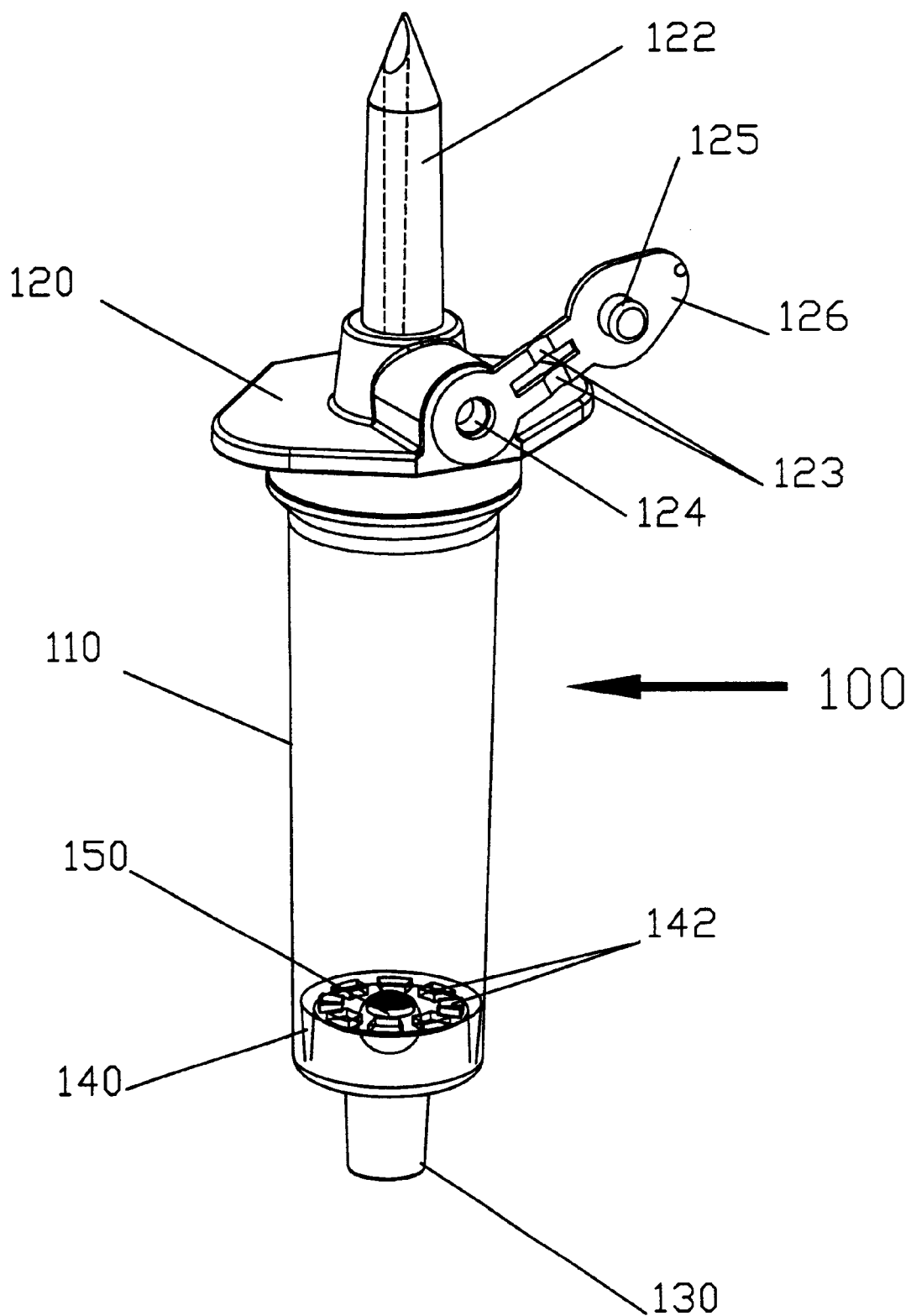
FIG. 2 is a perspective view of the spike and drip chamber assembly of the present invention.
Figure 3:
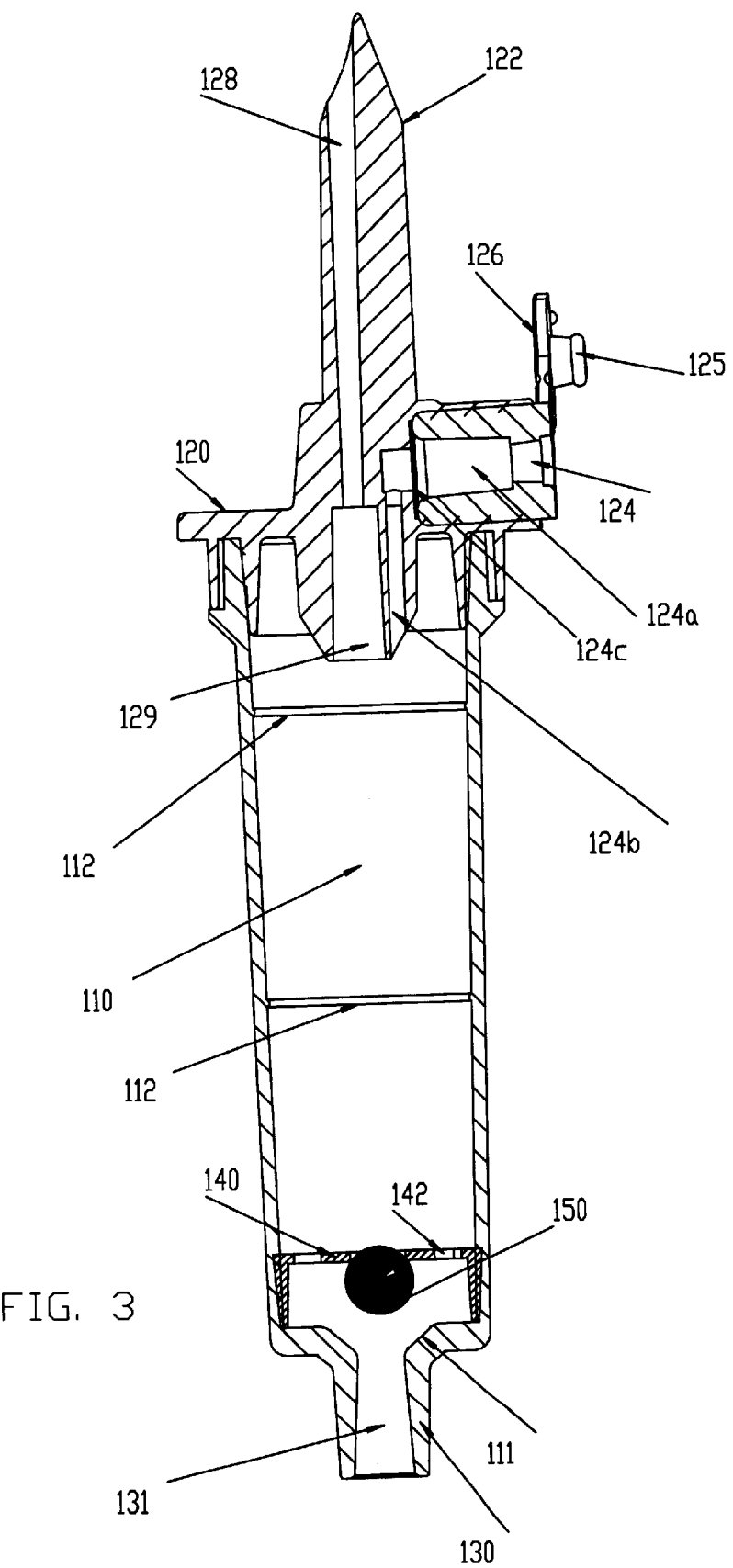
FIG. 3 is a plan view in cross section of the preferred embodiment of the present invention showing the floating ball in the open position.
Figure 4:
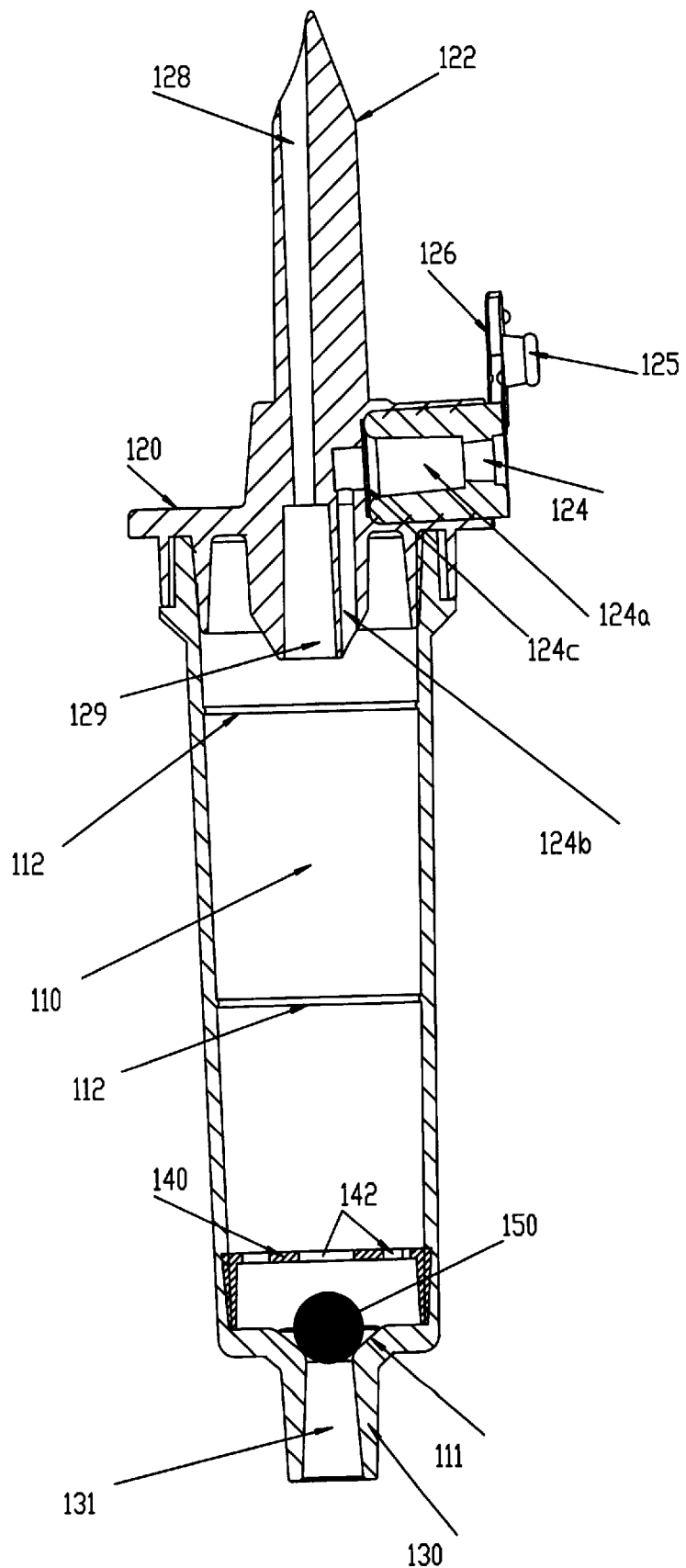
FIG. 4 is a plan view in cross section of the preferred embodiment of the present invention showing the floating ball in the closed position.
Figure 5:
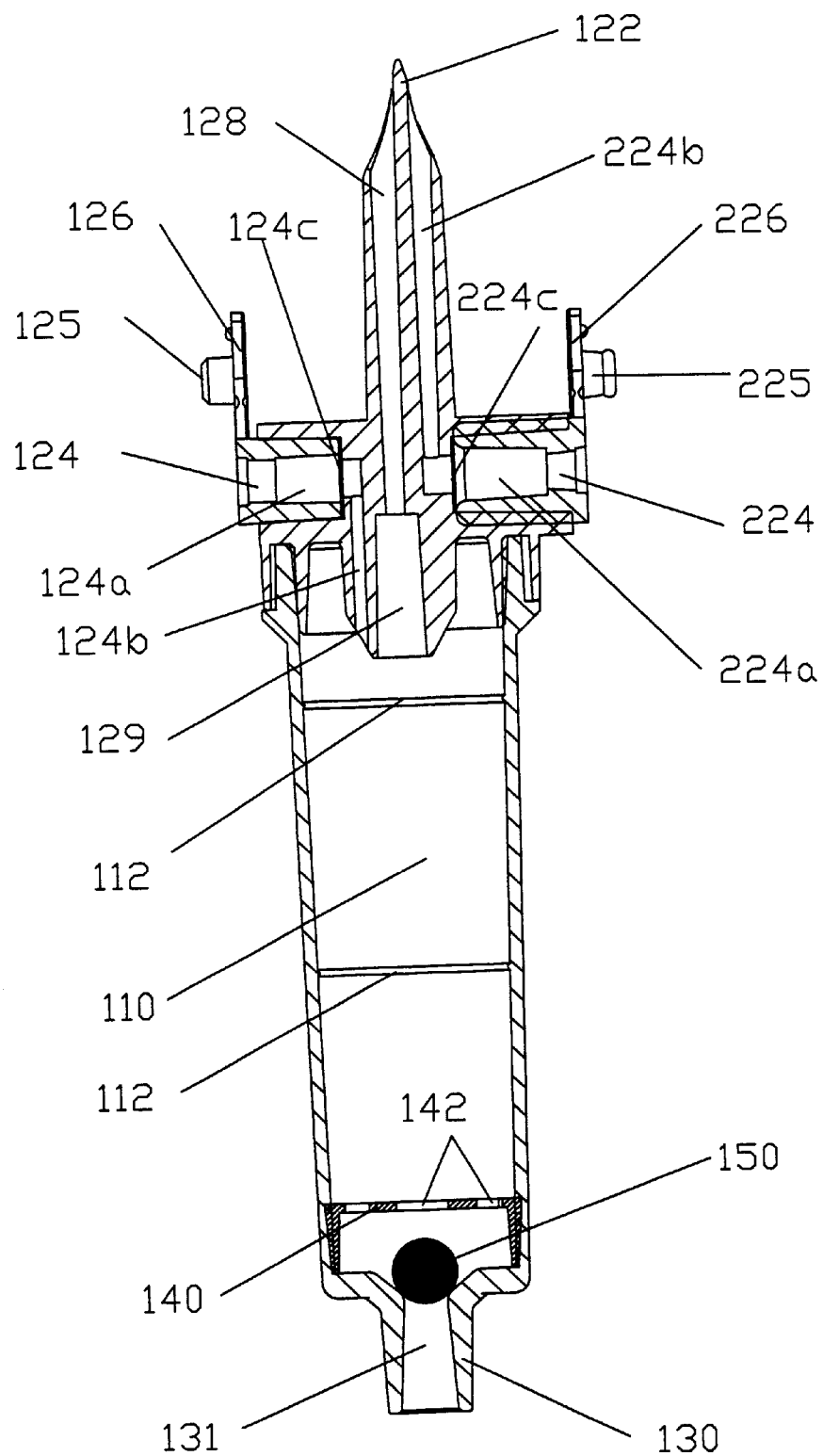
FIG. 5 is a plan view in cross section of a second embodiment having a vent in the spike from the atmosphere into the container.

Referring now to FIGS. 2–4 the details of the IV spike and drip chamber assembly of the present invention are shown. The assembly 100 is seen to comprise a clear generally tubular drip chamber 110 with a spike 120 at the upper end and a tubular connector 130 at the lower end. Calibration marks 112 are included on the walls of the drip chamber. The spike 120 includes the puncture tip 122 and an air vent inlet 124. A fluid flow channel 128 passes through the puncture tip 122 and expanded chamber 129 and into the drip chamber 110. An air vent cap 126 is connected to the spike 120 by straps 123 and secured about the vent inlet. The inlet 124 leads to passageway 124a and thence at a right angle to passageway 124b and thence to the drip chamber 110. A microporous filter 124c is placed in passageway 124a to prevent bacteria and other contaminants from entering the drip chamber 110 when the vent 124 is open. The air vent cap 126 includes a plug 125 which fits into the inlet 124. At the lower end of the drip chamber 110 is a floating ball limiter in the form of a spider flange 140 having an opening slightly smaller than the diameter of the floating ball 150 which retains a floating ball 150 in place. The spider flange 140 also includes openings 142 through which the fluid may flow. The floating ball 150 has a density less than that of the fluid such that it will float in the fluid within the drip chamber 110. In FIG. 3 the floating ball 150 is shown floating in the fluid and resting against the spider flange 140.

In FIG. 4 the floating ball 150 is shown resting against the seat 111 over the outlet 131 which seals the chamber.

In a second embodiment the spike includes a second vent 224 to allow air to enter the container and displace the fluid as it is removed. The second vent is necessary for rigid containers such as jars as otherwise a vacuum would be created above the fluid as it drains from the container eventually preventing flow. The second vent 224 is similar to first in having a vent cap 226 which is attached to the vent by straps 223 and having plug 225 which fits into vent opening to seal the vent. Passageway 224a leads to passageway 224b which leads upward through puncture tip 122 and into the container (not shown). A second microporous filter 224c is placed in passageway 224a to prevent bacteria and other contaminants from entering the container when the vent 224 is open.

In operation the vent inlet 124 is closed by the vent cap 126 and the puncture tip 122 is inserted through the puncture pad of the initial IV fluid container and fluid allowed to flow into the drip chamber to the desired level. Air is removed from the tubing attached to the tubular connector 130 and the tubing attached to the catheter which, if not already in the patient's vein may now be inserted. When the IV bag and drip chamber empties the floating ball 150 floats downward until it settles on the seat 111 which seals the drip chamber 110. The puncture tip 122 is removed from the empty IV fluid container and placed into a new full container. The vent cap 126 is removed from the vent inlet 124 and air is removed from the drip chamber 110 and the chamber filled to the desired level. Thus no air enters the tube which remains full from the previous bag, the floating ball 150 preventing air from entering the tube from the empty drip chamber 110.

What is claimed is:

1. An intravenous container spike for administering a medicinal fluid from a source, comprising:

(a) a drip chamber having a fluid outlet at the lower end with a seat over said outlet;

(b) a spike at the upper end of said drip chamber, said spike having a puncture tip at the upper end with a fluid channel through said puncture tip into said drip chamber;

(c) a floating ball in said drip chamber having a density less than said medicinal fluid such that said floating ball floats in said medicinal fluid so that as the fluid level in said drip chamber decreases said ball settles onto said seat sealing said outlet;

(d) a first sealable vent in said spike to allow air to be expelled from said drip chamber, said sealable vent comprising a vent inlet, an air passageway into said drip chamber and a vent cap attached to said inlet to seal said vent inlet;

(e) a spider flange located in the lower end of said drip chamber to limit the upper movement of said floating ball; and (f) a second sealable vent in said spike to allow air to enter said container through said puncture tip.

2. The intravenous container spike according to claim 1 further comprising:

(g) a first microporous filter in said first sealable vent; and (h) a second microporous filter in said second sealable vent.

* * * * *